(12) United States Patent
Fu et al.

(10) Patent No.: US 6,235,495 B1
(45) Date of Patent: May 22, 2001

(54) METHODS FOR THE QUANTITATION OF OXIDIZED GLUTATHIONE

(75) Inventors: Min-Xin Fu, Vancouver; Dennis M. Murray, Ridgefield, both of WA (US)

(73) Assignee: Oxis International, Inc., Portland, OR (US)

( * ) Notice: Subject to any disclaimer, the term of this patent is extended or adjusted under 35 U.S.C. 154(b) by 0 days.

(21) Appl. No.: 09/439,215

(22) Filed: Nov. 12, 1999

(51) Int. Cl.7 .............................................. C12Q 1/26
(52) U.S. Cl. ....................................................... 435/25
(58) Field of Search ............................ 435/25, 7.7, 7.8, 435/7.93, 7.94

(56) References Cited

U.S. PATENT DOCUMENTS 5,543,298    8/1996  Xu et al. .

OTHER PUBLICATIONS

Griffith, O. W. Determination of Glutathione and Glutathione Disulfide Using Glutathione Reductase and 2–Vinylpyridine; Anal. Biochem. 106, 207–212, 1980.*
Tietze, 1969, Analytical Chem. 27:502–22.
Guntherberg et al., 1966, Anal. Biochem. 15:205–10.
Griffith, 1980, Anal. Biochem. 106:207–212.

* cited by examiner

Primary Examiner—Jon P. Weber
Assistant Examiner—Patricia Patten
(74) Attorney, Agent, or Firm—Klauber & Jackson

(57) ABSTRACT

The present invention is directed to a method for determining the level of oxidized glutathione, or the ratio of reduced glutathione to oxidized glutathione, in a biological sample utilizing the thiol scavenging reagent 1-methyl-2-vinylpyridinium trifluoromethanesulfonate or another salt thereof at a level which rapidly scavenges reduced glutathione but does not interfere with the measurement of oxidized glutathione.

8 Claims, 1 Drawing Sheet

METHODS FOR THE QUANTITATION OF OXIDIZED GLUTATHIONE

FIELD OF THE INVENTION

The present invention is directed to a method for determining the level of oxidized glutathione (GSSG), or the ratio of reduced glutathione (GSH) to oxidized glutathione, in a biological sample utilizing the scavenger reagent 1-methyl-2-vinylpyridinium trifluoromethanesulfonate or another salt thereof at a level which rapidly scavenges GSH but does not interfere with the measurement of GSSG.

BACKGROUND OF THE INVENTION

The state of oxidative stress is a balance between prooxidant and antioxidant mechanisms. Increased oxidative stress is associated with various diseases such as coronary heart disease, neurodegenerative diseases, arthritis, and cataract formation. Antioxidant mechanisms exist in the body such as antioxidant enzymes and other small molecular antioxidants that can protect against harmful effects of free radicals. Among these, glutathione (GSH) is major antioxidant in human tissues, particularly in erythrocytes. Glutathione is a tripeptide with a free thiol group. Under the effect of glutathione peroxidase, GSH can remove $H_2O_2$ at a high rate and in the process itself becomes oxidized glutathione (GSSG). The GSSG must then be converted back to GSH by the enzyme glutathione reductase. When erythrocytes are exposed to the increased oxidative stress, the ratio of GSH/GSSG will decrease, particularly evident in erythrocytes, as a consequence of GSSG accumulation. Therefore, the measurement of the GSH/GSSG ratio provides a significant index to evaluate the state of oxidative stress.

Since Tietze (1) developed an enzymatic method for quantitative determination of amounts of total and oxidized glutathione, the estimation of total glutathione in human tissues have been very successful. The method employs Ellman's reagent (5,5'-dithiobis-2-nitrobenzoic acid), which reacts with GSH to form a spectrophotometrically detectable product. GSSG may be determined by reduction of GSSG to GSH with glutathione reductase and a reductant such as NADPH (β-nicotinamide adenine dinucleotide phosphate, reduced form), and reaction of formed GSH (and any GSH in the original sample) with Ellman's reagent.

However, the accurate measurement of tissue GSSG levels has proved very difficult due to either the lower amount of this form in tissue, or because of the absence of effective methods to prevent oxidation of GSH to GSSG during the process of sample preparation. In order to measure the GSSG in tissue, Guntherberg and Rost (2) first introduced N-ethylmaleimide (NEM) to eliminate the GSH. Although NEM can react with GSH to form a stable complex and prevent the participation of the reduced form in the enzymatic assay, NEM also inhibits glutathione reductase. Therefore, NEM must be removed from the sample before enzymatic assay. For this reason, Griffith (3) first introduced 2-vinylpyridine (2-VP) to derivatize GSH, since 2-vinylpyridine does not inhibit glutathione reductase significantly. Although 2-VP can react with GSH, it is a slowly reactive reagent and has little solubility in aqueous medium. The reaction usually takes about 60 min to remove 70% GSH in the sample with 10 mM 2-VP, during which time oxidation of GSH may occur, obscuring the level of GSSG. Furthermore, 2-VP interferes with the glutathione reductase method to some extent. To date, many reports indicate that the GSSG level in normal blood is up to 50 mM, which might be significantly overestimated by oxidation of GSH in samples, particularly in a red blood cell lysate, to GSSG in the absence of optimal sample preparation procedures to prevent formation of GSSG.

French patent application Serial No. 91.14782 (PCT/FR92/01093; U.S. Pat. No. 5,543,298) identifies 1-methyl-2-vinylpyridinium trifluoromethanesulfonate (M2VP); 1,4,6-trimethyl-2-vinylpyridinium tetrafluoroborate (TM2VP); and 1-methyl-4-vinylquinolinium tetrafluoroborate (M4VP) as mercaptan scavenging compounds useful for assaying superoxide dismutase activity.

It is toward the development of a method to quantitate levels of GSSG by preventing oxidation of GSH in a sample and permitting the measurement of GSSG that the present invention is directed.

The citation of any reference herein should not be construed as an admission that such reference is available as "Prior Art" to the instant application.

SUMMARY OF THE INVENTION

In its broadest aspect, the present invention is directed to a method for determining the level of oxidized glutathione (GSSG) in a biological sample comprising the steps of first collecting the sample in the presence of a sufficient amount of 1-methyl-2-vinylpyridinium (M2VP) trifluoromethanesulfonate, or another salt thereof, to rapidly scavenge substantially all reduced glutathione (GSH) in the sample, and permit the quantitation of GSSG in the sample using a glutathione reductase method. The biological sample may be, for example, whole blood, plasma, serum, lymphatic fluid, cerebrospinal fluid, saliva, tears, urine, cells or tissue, are sources of samples for the assay herein. The amount of M2VP is sufficient to rapidly scavenge GSH in the sample but does not interfere with the measurement of GSSG using glutathione reductase in the assay. The M2VP or another salt thereof is present at a final concentration of about 2 mM to about 5 mM, preferably at a final concentration of about 3 mM.

A further aspect of the present invention is a method for determining the ratio of the GSH to GSSG in a biological sample by (1) determining the level of GSSG in said sample in accordance with the method described above; (2) determining the level of total glutathione in the sample using a glutathione reductase method, and from the two aforementioned levels, determining the ratio.

The aforementioned methods may be used for determining the level of oxidative stress in an individual. The level of oxidative stress may be associated with a disease, and used to identify patients at risk for the development of the disease, or monitor therapies directed to the disease. Diseases associated with increased oxidative stress include but are not limited to coronary heart disease, neurodegenerative diseases, arthritis, and cataract formation.

These and other aspects of the present invention will be better appreciated by reference to the following drawing and Detailed Description.

DETAILED DESCRIPTION OF THE INVENTION

Figure 1:
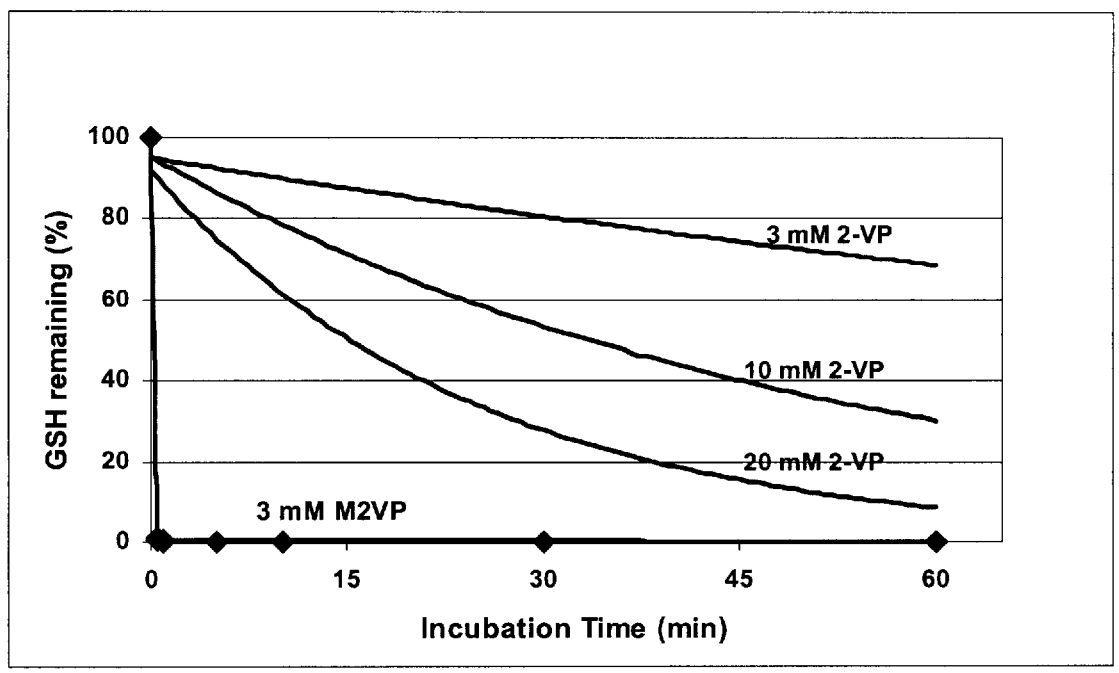
FIG. 1 compares the removal of GSH by 1-methyl-2-vinylpyridinium trifluoromethanesulfonate to that of 2-vinylpyridine.

In order to use a feasible method to accurately determine the amount of oxidized glutathione (GSSG) in fresh tissue, particularly in whole blood, it is necessary to treat the sample immediately after it is taken from the body to prevent any reduced glutathione (GSH) in the sample to be oxidized artifactually to elevate GSSG levels. After such treatment, treated samples may be stored for later determination of GSSG by standard methods. For determining the ratio of GSH to GSSG in a biological sample, treated and untreated aliquots of the sample may be stored and the GSH/GSSG levels determined in each, permitting the expression of the ratio. However, previously described reagents capable of scavenging GSH suffered from one or a combination of deficiencies including an insufficient rapidity of reacting with GSH in the sample, allowing some to become oxidized to GSSG, or the scavenging reagent interfering with the subsequent detection of GSH and/or GSSG in the sample by interfering with the activity of the enzyme used to perform the assay, glutathione reductase. The previously-described reagents for this use, M4VP, can inhibit glutathione reductase to some extent, and TM2VP has relative weak scavenging activity toward GSH.

It has been discovered by the inventors herein that the compound, 1-methyl-2-vinylpyridinium (M2VP) trifluoromethanesulfonate, or another salt thereof, in contrast to other related compounds with known GSH scavenging activity, may be used to overcome the aforementioned problems in accurately determining GSSG levels or GSH/GSSG levels, and overcomes the deficiencies in the prior art. A level of M2VP may be selected which rapidly scavenges GSH from a biological sample, but is not sufficient to interfere with the glutathione reductase method.

In a typical example of the procedure for determining the level of GSSG in a biological sample, the fresh sample immediately mixed with a solution containing M2VP. For example, 10 volumes of sample if mixed with one volume of 33 mM M2VP, provides a final concentration of 3 mM M2VP. Complete scavenging of GSH is completed within about one minute, substantially eliminating the artifactual elevation of GSSG through oxidation of GSH in the sample. The sample may be stored until completing the assay, for example at −70° C. When the GSSG level is to be determined, the sample is thawed, and the sample treated for assay using the glutathione reductase method. Typically, proteins in the sample may be removed by adding metaphosphoric acid, trichloroacetic acid, 5-sulfosalicylic acid or other deproteinating acid, preferably metaphosphoric acid, to the sample, and centrifuging out the precipitated proteins. The supernatant solution is diluted and used for the assay as reported by Tietze (1). The GSSG level is calculated from the spectrophotometric determination of the reaction of Ellman's reagent with GSSG, taking into account the dilution factor of the original sample. The invention herein is not, however, limited to the method of determining GSSG levels.

If GSH is also being assayed, or the GSH to GSSG ratio, a sample not treated with the scavenging agent is collected and stored frozen until the assay is to be performed. At that time, this untreated sample may be thawed, and treated in an identical manner to that sample treated with the scavenger. The glutathione reductase method from this sample yields the total of GSH and GSSG. As the treated sample provides the level of GSSG, the amount of GSH or the ratio of GSH to GSSG may be calculated from the results of the two assays.

The glutathione reductase method described herein refers to the assay for GSH and/or GSSG which employs glutathione reductase as the means for reducing GSSG in the sample to GSH, with the appropriate reductant such as NADPH which the reacts with a chromogen, such as Ellman's reagent, to produce a color. Such assays have been described, such as by Tietze (1), and are known to one of skill in the art. The invention herein is not so limiting to the method of determining the GSH and/or GSSG level, or their ratio, by the use of glutathione reductase in the assay. In brief, the method of Tietze (1), herein incorporated by reference, utilizes the change in absorbance (color development) at 412 nm during the reaction with glutathione reductase, reductant, and Ellman's reagent, compared to a standard curve. The reaction rate is proportional to the total GSH and GSSG level.

The preferred salt form of the scavenger compound is the trifluoromethanesulfonate, but other suitable salts are embodied herein, such as the trifluoroborate salt. The compound may be prepared by the methods described in French patent application Serial No. 91.14782 (PCT/FR92/01093; U.S. Pat. No. 5,543,298).

As used herein, the term "levels" and equivalent terms as relate to GSSG and GSH refer to the levels of these substances as present in circulation, in tissues, etc. As described in the Background section above, the measure of the GSSG level or the GSH/GSSG level is diagnostically useful as a measure of oxidative stress. As previously noted, various disease processes are etiologically related to oxidant levels in the body, particularly to elevated levels, and therapeutic utility of antioxidant compounds to counteract these deleterious effects has recently become an important area for the development of prophylaxes and treatments for these disorders and diseases. Moreover, exercise increases oxidative stress in the body. Both the measurement of the GSH/GSSG ratio as an indicator of the oxidative stress of the individual, the diagnosis of abnormally elevated levels of oxidants, and monitoring effectiveness of therapies to return elevated levels to normal or to reduce levels below normal as prophylactic measures, are embodied within the uses of the methods described herein.

Various sources of biological samples are embraced herein. A preferred sample is whole blood, for ease in collection and as an indicator of oxidant levels within the body. The baseline levels of GSSG in intact red blood cells can be stable up to 24 hours at 4° C., but increase within a few minutes in red blood cell lysates. Other bodily fluids such as lymphatic fluid, cerebrospinal fluid, saliva, tears, and urine, are sources of samples for the assay herein. Solid tissue samples such as those obtained by biopsy, dissection, or scrapings for example from the lining of the inside of the cheeks, may be used as sources of material. The present invention is not limited to the source of the sample. Sources from mammals other than humans, animals other than mammals, plants, fungi, protists, other living organisms which contain GSH are embraced herein as sources for determination of GSH, GSSG, GSH:GSSG ratio, and oxidative stress.

The methods of the invention for determining GSSH levels of the GSSH/GSH ratio may be used for the prophylaxis, treatment or monitoring of various diseases associated with increased oxidative stress, such as, but not limited to, coronary heart disease, neurodegenerative diseases, arthritis, and cataract formation. The skilled artisan is aware of may other conditions and diseases known to be directly or indirectly associated with increased oxidative stress. As noted above, exercise is known to increase oxidative stress within the body. The assays herein may be used to test an individual, using a bodily fluid, cellular or tissue sample, as described above, to identify the level of oxidative stress. The individual may have a condition or disease associated with such increased levels, or be at risk for developing such conditions or diseases, or be interested in such levels, and in prophylaxis to prevent their occurrence. Such information may be used to recommend changes in lifestyle, diet, medication, or other factors to reduce the level of oxidative stress. The ability of the individual to cope with increased oxidative stress, such as results from exercise, may be readily determined by the methods described herein. Compliance and/or success at such prophylaxis or therapy may be monitored by periodically monitoring oxidative stress by the methods herein.

The present invention may be better understood by reference to the following non-limiting examples, which are provided as exemplary of the invention. The following examples are presented in order to more fully illustrate the preferred embodiments of the invention. They should in no way be construed, however, as limiting the broad scope of the invention.

EXAMPLE 1

Efficiency of Scavenging of GSH by M2VP

The scavenging activity and assay detectability of M2VP was evaluated by reacting GSH with M2VP to a final concentration of 3 mM, followed by measurement of GSH and/or GSSG in a glutathione reductase method assay. Table 1 shows the scavenging activity of M2VP on GSH.

TABLE 1

| Sample | GSH [$\mu$M] remaining (%) | GSH |
|---|---|---|
| GSH alone | 747 | 100 |
| GSH + 3 mM M2VP (1-min incubation) | 1.49* | 0.20 |
| GSH + 3 mM M2VP (5-min incubation) | 1.65 | 0.22 |
| GSH + 3 mM M2VP (60-min incubation) | 1.58 | 0.21 |

* This small amount of GSSG might derive from the reagent contaminant.

These data show that the addition of M2VP substantially depletes the reaction of GSH.

EXAMPLE 2

Recovery of GSSG in the Presence of M2VP

In this experiment, the detectability of GSSG was determined in the absence or presence of M2VP at 10 mM and 100 mM. The results are shown in Table 2.

TABLE 2

| Sample | Rate at A412nm | Recovery (%) |
|---|---|---|
| GSSG alone | 0.0306 | 100.00 |
| GSSG + 10 mM M2VP | 0.0299 | 97.71 |
| GSSG + 10 mM M2VP | 0.0313 | 102.29 |
| GSSG alone | 0.0208 | 100.00 |
| GSSG + 100 mM M2VP | 0.0206 | 99.04 |
| GSSG + 100 mM M2VP | 0.0201 | 96.63 |

The data in Table 2 show that the concentration of M2VP up to 10 mM does not interfere with the detectability of GSSG in the sample; at 100 mM some interference occurs. Further studies demonstrated that mixing a whole blood sample with M2VP at a final concentration of 3 mM eliminated more than 99.7% of GSH in the sample, without interfering with the detectability or recovery of GSSG in the assay.

EXAMPLE 3

Sample Preparation for GSH and GSSG Determinations

The following is an example of a sample preparation procedure for preparing whole blood samples for determinations of total GSH and GSSG and for determination of GSSG alone using the scavenging reagent of the present invention. To prepare a sample of whole blood for total GSH and GSSG: 100 $\mu$l whole blood is added to 300 $\mu$l 5% metaphosphoric acid (MPA). The tube is mixed by vortexing for 15–20 sec., then centrifuged at >2,000 rpm for 5 min. The aqueous layer (extract) is collected, and 50 $\mu$l of the extract is added to 1450 $\mu$l of Tietze buffer for carrying out the assay. The extract must be frozen at less than −20° C. until assayed. The above procedure results in a 120-fold dilution of the sample.

To prepare whole blood for GSSG measurement alone: 100 $\mu$l freshly collected blood is mixed with 10 $\mu$l of 33 mM M2VP. After gentle mixing, the sample must be frozen at −70° C. until used. After thawing at room temperature for 10 min., 300 $\mu$l of 5% MPA is added, and the mixture is mixed by vortexing for 15-20 sec., and the precipitated materials centrifuged at $\geq$2,000 rpm for 5 min. The supernatant (extract) is collected, and 50 $\mu$g of extract combined with 700 $\mu$l of Sample buffer (1:15 dilution) for GSSG determination. The total dilution is 60-fold.

The total GSSG and GSH assay is carried out on each sample, according to standard procedures. The M2VP-treated sample provides a measure of GSSG only; that of the sample not treated with the scavenger provides a measure of total GSH and GSSG. By subtracting the latter from the former, the amount of GSH is obtained. The results can be expressed as the ratio of GSH to GSSG.

Of course, the above procedure utilizing the scavenger only can be used to determine GSSG alone in a sample, if the GSH or ratio information is not needed for the particular application.

EXAMPLE 4

Measurement of GSH and GSSG in whole human blood Using the procedures described in Example 3 above, GSH:GSSG ratios were determined on fresh human blood samples from three subjects before and after exercise. The results of the assay are shown in Table 3.

TABLE 3

| Sample | GSH [$\mu$M] | GSSG [$\mu$M] | [GSH]/[GSSG] |
|---|---|---|---|
| No. 1 (before) | 752 | 1.78 | 422.47 |
| No. 1 (after) | 738 | 2.56 | 288.28 |
| No. 2 (before) | 880 | 1.61 | 546.58 |
| No. 2 (after) | 913 | 2.01 | 454.23 |
| No. 3 (before) | 897 | 1.76 | 509.66 |
| No. 3 (after) | 924 | 2.66 | 347.37 |

These results show that the ratios of GSH/GSSH decreased after exercise in all three subjects, indicating the exercise increased the oxidative stress of the subject.

EXAMPLE 5

Removal of GSH by 1-methyl-2-vinylpyridinium trifluoromethanesulfonate vs. 2-vinylpyridine.

Three concentrations of 2-VP (3, 10 or 20 mM) or 3 mM M2VP were added into GSH solutions, and then incubated at room temperature for various time points. After incubation, each sample was measured by the glutathione reductase method for the remaining GSH. The result, in FIG. 1, show that 3 mM M2VP eliminates 99.7% GSH, but only 11.7% for 3 mM 2-VP, within one minute. There still is 8.98% GSH remaining when 2-VP, at a concentration of up to 20 mM and incubated for 60 minutes, is used. These results indicated that M2VP has much stronger GSH scavenging activity compared 2-VP.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

REFERENCES

1. Tietze F (1969): Analytical Chemistry 27, 502–522.
2. Guntherberg H and Rost J (1966): Anal. Biochem. 15, 205–210.
3. Griffith O W (1980): Anal. Biochem. 106, 207–212.

What is claimed is:

1. A method for determining the level of oxidized glutathione in a biological sample comprising the sequential steps of:

A. collecting said sample in the presence of a sufficient amount of a 1-methyl-2-vinylpyridinium salt to rapidly scavenge substantially all reduced glutathione in said sample and permit the quantitation of oxidized glutathione in said sample using a glutathione reductase method; and B. quantitating said oxidized glutathione in said sample using a glutathione reductase method.

2. The method of claim 1 wherein said biological sample is whole blood, serum, plasma, lymphatic fluid, cerebrospinal fluid, saliva, tears, urine, cells or tissues.

3. The method of claim 2 wherein said biological sample is whole blood.

4. The method of claim 1 wherein said sufficient amount of a 1-methyl-2-vinylpyridinium trifluoromethanesulfonate salt does not interfere with the measurement of oxidized glutathione using a glutathione reductase method.

5. The method of claim 4 wherein said 1-methyl-2-vinylpyridinium salt is present at a final concentration of about 2 mM to about 5 mM.

6. The method of claim 5 wherein said 1-methyl-2-vinylpyridinium salt is present at a final concentration of about 3 mM.

7. The method of claim 1 wherein said 1-methyl-2-vinylpyridinium salt is 1-methyl-2-vinylpyridinium trifluoromethanesulfonate or 1-methyl-2-vinylpyridinium trifluoroborate.

8. A method for determining the ratio of the levels of reduced glutathione to oxidized glutathione in a biological sample comprising determining the level of oxidized glutathione in said sample in accordance with claim 1; determining the level of total oxidized and reduced glutathione in said sample using a glutathione reductase method, and from said levels determining said ratio.

\* \* \* \* \*